United States Patent [19]

Möller et al.

[11] Patent Number: 4,496,536

[45] Date of Patent: Jan. 29, 1985

[54] SEBOSUPPRESSIVE COSMETIC PREPARATIONS CONTAINING LONG-CHAINED ALKANOLS AND ANTIOXIDANTS

[75] Inventors: Hinrich Möller; Siegfried Wallat, both of Monheim; Horst Höffkes, Düsseldorf; Karl Giede, Hilden, all of Fed. Rep. of Germany

[73] Assignee: Henkel Kommanditgesellschaft auf Aktien, Düsseldorf-Holthausen, Fed. Rep. of Germany

[21] Appl. No.: 372,474

[22] Filed: Apr. 28, 1982

[30] Foreign Application Priority Data

Jan. 20, 1982 [DE] Fed. Rep. of Germany ....... 3201511

[51] Int. Cl.$^3$ .......................... A61K 7/06; A61K 7/08; A61K 31/05; A61K 31/355
[52] U.S. Cl. ...................................... 424/70; 252/522; 424/DIG. 4; 424/47; 514/852; 514/458; 514/731; 514/544
[58] Field of Search ................... 424/70, DIG. 4, 284, 424/346, 308

[56] References Cited

U.S. PATENT DOCUMENTS 3,903,257 9/1975 Arai et al. ..................... 424/DIG. 4
4,172,123 10/1979 Lowicki ................................ 424/67

FOREIGN PATENT DOCUMENTS 2144249 3/1972 Fed. Rep. of Germany ...... 424/284
1089353 9/1954 France ................................ 424/358

OTHER PUBLICATIONS

Lesser, Drug and Cosmetic Industry, 3/1952, No. 70, No. 3, pp. 320, 321 and 420 to 425.
Whalley, Amer. Perf. and Cosm., 8/1967, vol. 82, No. 8, pp. 47 to 49.

Primary Examiner—Dale R. Ore
Attorney, Agent, or Firm—Hammond & Littell, Weissenberger & Dippert

[57] ABSTRACT

This invention relates to a topical cosmetic preparation for treating oily hair or seborrhea which contains a sebosuppressively effective amount of at least one long-chain alkanol and at least one antioxidant.

4 Claims, No Drawings ns. More particularly, this invention relates to topical cosmetic preparations useful in treating oily hair and seborrheic skin.

BACKGROUND OF THE INVENTION

Excessive excretion of the sebaceous glands in the scalp gives hair an oily appearance that generally is considered esthetically unappealing. Consequently, there have been many attempts to make such glands secrete normally by suitable means, to restore a healthy look to the hair. Cosmetic preparations containing sulfur, mercury, or tar have been used to fight seborrhea on the head. It has been found that these known anti-seborrheic additives frequently lead to side effects after prolonged use, without yielding really satisfactory results, as far as their effectiveness and application properties are concerned. German published patent application (DE-OS) No. 29 26 267 mentions 3,7,11-trimethyl-2,6,10-dodecatrien-1-ol derivatives as an additive to cosmetic preparations to normalize sebum secretion. However, it has been found that these compounds have a very low anti-seborrheic effect.

OBJECTS OF THE INVENTION

It is an object of the invention to provide topical cosmetic preparations.

It is also an object of the invention to provide topical cosmetic preparations useful in treating oily hair and seborrhea.

It is a further object of the invention to provide topical cosmetic preparations containing long-chain alkanols and antioxidants.

These and other objects of the invention will become more apparent in the discussion below.

DETAILED DESCRIPTION OF THE INVENTION

Applicants have now discovered topical cosmetic preparations which are especially effective in the treatment of seborrhea and strongly oily hair. These topical cosmetic preparations contain long-chain alkanols and antioxidants, even in very small amounts. More particularly, the useful alkanols have from about 12 to 26 carbon atoms and may optionally contain one or more carbon-carbon double bonds. Long-chain alkanols having one or more branches in the molecule are preferred. Examples of highly suitable alkanols include 2-methylundecanol, 2-methyldodecanol, 2-methyltetradecanol, 2-butyloctanol, 2-hexyldecanol, 2-octyldodecanol, (Eutanol®G, available from Henkel), isooctadecyl alcohol, 2-(1,3,3-trimethylbutyl)-5,7,7-trimethyloctanol, farnesol, and phytol.

Any of the known antioxidants can be used according to the invention. However, particularly useful antioxidants include 2,6-di-tert.butyl-4-methylphenol (BHT), 2,6-di-tert.butyl-4-methoxyphenol (BHA), tocopherols (Vitamin E) such as, for example, d,1-α-tocopherol, and alkyl esters of gallic acid.

The above-mentioned alkanols and antioxidants are commercially available. The sebosuppressive, i.e., anti-seborrheic, combination of action substances is well tolerated by the skin and mucous membranes, and can be easily incorporated into various cosmetic preparations, such as aqueous, alcoholic, or aqueous alcoholic solutions, oils, suspensions, gels, emulsions, ointments, pastes, or aerosols. For the treatment of seborrhea and oily hair, these combinations of active ingredients can be used in all conventional application forms, such as, hair tonics, hair shampoos, hair treatments, hair rinses or skin lotions. Use in hair cosmetics is preferred. In addition to the combination of active substances according to the invention, these cosmetic preparations can contain known vehicles and additives such as water, organic solvents, surface-active compounds, oils, fats, waxes, perfume, dyes, preservatives, and the like. The sebosuppressive topical cosmetic preparations of the invention contain at least one long-chain alkanol and at least one antioxidant in an amount sufficient to impart anti-seborrheic properties. The cosmetic preparations perferably contain from about 0.01 to 5.0 percent by weight, more preferably from about 0.05 to 1.0 percent by weight, based upon the total weight of the cosmetic preparation, of the alkanols and antioxidants, respectively. The weight ratio of long-chain alkanol to antioxidant is preferably from about 4:1 to 1:4, more preferably from about 2:1 to 1:2.

The following examples are intended to illustrate the invention and should not be construed as limiting it thereto.

EXAMPLES

Testing for Anti-seborrheic Activity

The anti-seborrheic activity of long-chain alkanols in combination with antioxidants was examined closely in the animal experiments described hereinafter. The experimental animals were male Wistar rats weighing from 220 to 230 gm. The degree of brown discoloration on the shaved backs of the rats was established visually; the brown discoloration was caused by the brown skin surface lipid of the rats. This test is based upon the observation that young female rats as well as male rats that were washed with tenside solution and a lipid solvent, respectively, as well as male rats that were trated systematically with estrogen, show only the normal light, pink skin after shaving; parallel to this, only relatively very small amounts of lipid can be extracted from the shorn hair.

For the evaluation of the anti-seborrheic activity, the test substances set forth in the table below, each in the form of a 1% solution in ethanol, were each brushed on one side of the back fur of 6 rats. The other side was treated only with the solvent without the active substance (control side). During the testing period of 14 days, application of test substance was made once a day on a total of 9 days. A group of 6 rats that remained completely untreated served as an additional control. At the end of the testing, the animals were shaved on the back and the flanks and inspected visually, this inspection being done independently by an evaluation panel (6 persons) under double-blind conditions.

Evaluation methods

Three criteria were rated. The first criterion was whether the majority of the evaluators recognized the treated side properly. The differentiations were as follows:

| Symbol | Percentage of evaluators recognizing an effect |
| --- | --- |
| + + | 100% |
| + | >50% to <100% |
| 0 | ≦50% |

The second criterion was the difference between the right and left side, one point each to be given per evaluator and animal, in the manner that the darker side was rated 1 and the lighter side 0 and that the uniformity of both sides was rated 0.5.

Significant differences between the untreated and the treated side according to the second method of evaluation indicate the topical effectiveness of a substance.

The third criterion was the rating of the difference in intensity of the brown shades according to the following scale:
dark brown: 3 points
medium brown: 2 points
light brown: 1 point
no brown coloration: 0 points According to the third method of evaluation, the differences in the point totals between the untreated control animals and the treated and untreated sides, respectively, of the experimental animal group were calculated where significant differences between control animals and the treated side of the experimental animals indicate the effect of a substance. Similarly, a distinct difference between the untreated and the treated side of the experimental animal groups is also generally noticeable. However, this is not always as distinct as that between control animals and treated side, which may be due to various reasons, as, for example, mechanical transfer of substance from one side to the other or solvent influence.

The differentiation of the effects according to the methods of evaluation 2 and 3 was characterized in the following manner:

| Symbol | Difference in points |
| --- | --- |
| + + | very great (>99.9% probability) |
| + | significant (≧95% probability) |
| (+) | distinct, but <95% probability |

The results of the evaluations of the test substances according to the above-mentioned methods are set forth in the table below. In addition, the percentage of sebum reduction was calculated by dividing the point difference ($\Delta P$) by the number of points for the control group ($P_k$) and multiplying by 100%, as follows:

Sebum reduction $= \Delta P / P_k \times 100\%$.

TABLE

| Substance: | 1 | 2 | 3 | 4 | 5 | 6 | 7 | 8 | 9** | 10** | 11** | 12** | 13** | 14** | 15** |
| --- | --- | --- | --- | --- | --- | --- | --- | --- | --- | --- | --- | --- | --- | --- | --- |
| BHT* | 0.2 | 0.1 | — | — | — | — | — | — | 0.1 | 0.1 | — | 0.2 | — | 0.1 | 0.2 |
| d,l-α-Tocopherol* | — | — | 0.1 | — | — | — | — | — | — | — | 0.1 | — | 0.1 | — | — |
| Phytol* | — | — | — | 0.1 | — | — | — | — | 0.1 | — | — | — | — | — | — |
| Farnesol* | — | — | — | — | 0.1 | — | — | — | — | 0.1 | 0.1 | — | — | — | — |
| Eutanol ® G* | — | — | — | — | — | 0.1 | — | — | — | — | — | 0.1 | 0.1 | — | — |
| Isooctadecanol* | — | — | — | — | — | — | 0.1 | — | — | — | — | — | — | 0.1 | — |
| n-Hexadecanol* | — | — | — | — | — | — | — | 0.25 | — | — | — | — | — | — | 0.2 |
| Evaluation method: | | | | | | | | | | | | | | | |
| 1 | — | — | — | + | — | — | — | — | + + | + | + | + + | + + | + | + + |
| 2 | — | — | — | — | — | — | — | — | + + | + + | + + | + + | + + | + | + + |
| 3 | — | — | — | — | — | — | — | — | + + | + + | + + | + + | + + | + + | + + |
| Sebum reduction (%) | 0 | 0 | 0 | 0 | 0 | 0 | 0 | 0 | 83 | 42 | 33 | 31 | 35 | 28 | 35 |

*Parts by weight
**According to the invention

Examples of topical cosmetic preparations according to the invention for the treatment of strongly oily hair and seborrhea are as follows:

EXAMPLE 1

Shampoo for Oily Hair

| Component | Parts by Weight |
| --- | --- |
| Fatty alcohol ether sulfate with 28% by weight of wash active substance (Texapon ® N, available from HENKEL KGaA) | 42.5 |
| Ethanol amide of coconut fatty acid | 3.0 |
| Sodium chloride | 2.0 |
| Sodium sulfate | 2.0 |
| Phytol | 0.1 |
| d,l-α-Tocopherol | 0.1 |
| Perfume Oil | 0.1 |
| Water | 50.2 |
| | 100.0 |

EXAMPLE 2

Skin Cream

| Component | Parts by Weight |
| --- | --- |
| Self-emulsifying mixture of mono/diglycerides of higher saturated fatty acids with potassium stearate (Cutina ® KD 16, available from HENKEL KGaA) | 16.0 |
| Cetylstearyl alcohol with about 12 mols of ethylene oxide (Eumulgin ® Bl, available from HENKEL KGaA) | 1.0 |
| 2-Octyldodecanol | 6.0 |
| Isopropyl myristate | 4.0 |
| Glycerin | 6.0 |
| Farnesol | 0.1 |
| BHT | 0.2 |
| Water | 66.7 |
| | 100.0 |

EXAMPLE 3

Hair Treatment

| Component | Parts by Weight |
| --- | --- |
| Glycerin monostearate and distearate | 0.7 |

-continued

| Component | Parts by Weight |
| --- | --- |
| (Tegin ® M, available from Atlas Chemie) Cationic surfactant | 2.0 |
| Cholesterol | 0.2 |
| Soy lecithin | 0.3 |
| Emulsifier (Emulgade ® A, available from HENKEL KGaA) | 8.0 |
| 2-Octyl-dodecanol (Eutanol ® G) | 0.1 |
| BHT | 0.2 |
| Perfume | 0.3 |
| Water, desalinated | 88.2 |
| | 100.0 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for treating oily hair or seborrhea which comprises administering to an individual in need of such treatment a sebosuppressively effective amount of at least one branched, long-chain alkanol having from 12 to 26 carbon atoms and at least one antioxidant selected from the group consisting of 2,6-di-tert.-butyl-4-methoxyphenol, tocopherols, and alkyl esters of gallic acid, the weight ratio of long-chain alkanol to antioxidant being from about 4:1 to 1:4.

2. The process of claim 1, wherein the alkanol is selected from the group consisting of 2-methylundecanol, 2-methyltetradecanol, 2-butyloctanol, 2-hexyldecanol, 2-octyldodecanol, isooctadecyl alcohol, 2-(1,3,3-trimethylbutyl)-5,7,7-trimethyloctanol, farnesol, and phytol.

3. A process for reducing sebaceous cell sebum production in a mammal in need thereof which comprises contacting said sebaceous cell in the skin of said mammal with a sebosuppressively effective amount of a branched, long-chain alkanol having from 12 to 26 carbon atoms and at least one antioxidant selected from the group consisting of 2,6-di-tert.butyl-4-methoxyphenol, tocopherols, and alkyl esters of gallic acid, the weight ratio of long-chain alkanol to antioxidant being from about 4:1 to 1:4.

4. The process of claim 3, wherein the alkanol is selected from the group consisting of 2-methylundecanol, 2-methyltetradecanol, 2-butyloctanol, 2-hexyldecanol, 2-oxtyldodecanol, isooctadecyl alcohol, 2-(1,3,3-trimethylbutyl)-5,7,7-trimethyloctanol, farnesol, and phytol.

* * * * *

UNITED STATES PATENT AND TRADEMARK OFFICE
CERTIFICATE OF CORRECTION

PATENT NO. : 4,496,536
DATED : January 29, 1985
INVENTOR(S) : HINRICH MÖLLER et al.

It is certified that error appears in the above-identified patent and that said Letters Patent is hereby corrected as shown below:

Column 2, line 44, "trated" should read -- treated --.

Column 6, line 23, "2-oxtyldodecanol" should read
 -- 2-octyldodecanol --.

Signed and Sealed this

Twentieth Day of August 1985

[SEAL]

Attest:

DONALD J. QUIGG

Attesting Officer Acting Commissioner of Patents and Trademarks